US008802117B2

(12) United States Patent
Morganti

(10) Patent No.: US 8,802,117 B2
(45) Date of Patent: Aug. 12, 2014

(54) MELATONIN AND IMMUNOSTIMULATING SUBSTANCE-BASED COMPOSITIONS

(75) Inventor: Pierfrancesco Morganti, Aprilia (IT)

(73) Assignee: Mavi Sud S.r.l., Aprilia (IT)

( * ) Notice: Subject to any disclaimer, the term of this patent is extended or adjusted under 35 U.S.C. 154(b) by 974 days.

(21) Appl. No.: 12/281,523

(22) PCT Filed: Mar. 2, 2007

(86) PCT No.: PCT/EP2007/052026
§ 371 (c)(1),
(2), (4) Date: Oct. 14, 2008

(87) PCT Pub. No.: WO2007/099172
PCT Pub. Date: Sep. 7, 2007

(65) Prior Publication Data
US 2009/0162335 A1 Jun. 25, 2009

(30) Foreign Application Priority Data
Mar. 3, 2006 (IT) ............................. RM2006A0108

(51) Int. Cl.
*A61K 8/00* (2006.01)
*A61K 31/385* (2006.01)
*A61K 31/4045* (2006.01)
*A61K 45/06* (2006.01)
*A61K 31/07* (2006.01)
*A61Q 19/02* (2006.01)
*A61K 8/49* (2006.01)
*A61Q 19/08* (2006.01)
*A61Q 7/00* (2006.01)
*A61K 31/7016* (2006.01)
*A61K 31/505* (2006.01)

(52) U.S. Cl.
CPC .............. *A61K 8/492* (2013.01); *A61K 31/385* (2013.01); *A61K 31/4045* (2013.01); *A61K 45/06* (2013.01); *A61K 31/07* (2013.01); *A61Q 19/02* (2013.01); *A61Q 19/08* (2013.01); *A61Q 7/00* (2013.01); *A61K 31/7016* (2013.01); *A61K 31/505* (2013.01); *A61K 2800/522* (2013.01)
USPC ............................................ 424/401; 514/55

(58) Field of Classification Search
None
See application file for complete search history.

(56) References Cited

U.S. PATENT DOCUMENTS

| | | | |
|---|---|---|---|
| 5,985,293 A | 11/1999 | Tachon et al. | |
| 6,015,548 A * | 1/2000 | Siddiqui et al. | 424/59 |
| 6,974,841 B1 | 12/2005 | Rapisarda | |
| 2003/0157040 A1* | 8/2003 | Bunger et al. | 424/59 |
| 2004/0043963 A1* | 3/2004 | Wadstein | 514/55 |
| 2004/0185072 A1* | 9/2004 | Hitzel et al. | 424/401 |
| 2005/0271692 A1 | 12/2005 | Gervasio-Nugent et al. | |
| 2006/0014773 A1* | 1/2006 | McCleary | 514/283 |

FOREIGN PATENT DOCUMENTS

| | | | |
|---|---|---|---|
| DE | 101 10 418 | 9/2002 | |
| EP | 0 820 766 | 1/1998 | |
| WO | 00/53176 | 9/2000 | |
| WO | 00/57876 | 10/2000 | |
| WO | WO 2006/048829 | * 5/2006 | ............. A61Q 19/00 |

OTHER PUBLICATIONS

Min et al., Polymer 45, pp. 7137-7142, 2004.*
Buenger et al., Skin Pharmacology and Physiology, 2004; vol. 17, pp. 232-237.*
International Search Report for PCT/EP2007/052026 mailed Jun. 20, 2007.
Written Opinion for PCT/EP2007/052026 mailed Jun. 20, 2007.
International Preliminary Report on Patentability for PCT/EP2007/052026 completed May 5, 2008.
Lemon et al. "A dietary supplement abolish age-related cognitive decline in transgenic mice expressing elevated free radical processes" *Experimental Biology and Medicine*, vol. 228, pp. 800-810 (2003).
Morganti et al. "Role of topical and nutritional supplement to modify the oxidative stress" *International Journal of Cosmetic Science*, vol. 24, pp. 331-339 (2002).
Morganti et al. "Chitin-nanofibrils: A new active cosmetic carrier" *Journal of Applied Cosmetology*, vol. 26, No. 3, pp. 113-128 (Jul.-Sep. 2008).
Morganti et al. "New chitin complexes and their anti-aging activity from inside out" *Journal of Nutrition, Health & Aging*, vol. 16, No. 3, pp. 242-245 (2012).

* cited by examiner

*Primary Examiner* — Allison Ford
*Assistant Examiner* — Yvonne Pyla
(74) *Attorney, Agent, or Firm* — Nixon & Vanderhye PC

(57) ABSTRACT

The present invention relates to synergistic associations of melatonin and other active substances and cosmetic compositions suitable for treating all those manifestations causing or accompanying the aging of skin, hair and other tissues. In particular, the invention is based on the use of melatonin associated with immunoactive and antioxidant substances significantly potentiating its antiaging activity, remarkably reducing free radical formation and thereby improving the aspect of both skin and hair.

18 Claims, 11 Drawing Sheets

MELATONIN AND IMMUNOSTIMULATING SUBSTANCE-BASED COMPOSITIONS

This is the U.S. national phase of Intl Application No. PCT/EP2007/052026, filed 2 Mar. 2007, which designated the U.S. and claims priority to Italian Patent Application No. RM2006A000108 filed 3 Mar. 2006; the entire contents of each of which are hereby incorporated by reference.

FIELD OF THE INVENTION

The present invention relates to synergistic associations of active substances and cosmetic compositions suitable for treating all those manifestations causing or accompanying the aging of skin, hair and other tissues. In particular, the invention is based on the use of melatonin associated with immunoactive and antioxidant substances significantly potentiating its antiaging activity, remarkably reducing free radical formation and thereby improving the aspect of both skin and hair.

State of the Prior Art

It is known how free radicals (especially $O_2.-$) and other reactive Oxygen (radicals) species (ROS), like $H_2O_2$ and/or Nitric Oxide (NO) donors like the peroxynitrite anion are continuously produced in vivo, also at the level of the skin and of the cutaneous annexes.

Accordingly, also humans along their evolution have developed a defence system based on the production of antioxidants apt to protect the entire organism, as well as the skin and cutaneous annexes, from the aggressiveness of the ROS and NOS (Nitric Oxide Species). It is also known how humans possess a whole set of immune defence members, such as the Langerhans cells, the lymphocytes, the macrophages, as well as neuropeptides and neurohormones representing the first line of defence from attacks due to chemical agents, pollutants, UV rays, ozone and other foreign substances, also like bacteria, fungi, viruses.

All these aggressive environmental elements cause a continuous increase in the formation of free radicals (ROS and NOS). For these reasons, the system of physiological antioxidants engaged in tissue defence may drastically reduce, creating the conditions for an imbalance of the entire immune system (due, e.g., to UV-rays). As these delicate defence balances alter, there onset circumstances setting up the so-called oxidative stress.

As a consequence, a premature aging of skin and cutaneous annexes occurs, with appearance of wrinkles, formation of hyperpigmentary spots and reduction of hair number and volume. Moreover, oxidative stress can give rise to irritative forms and to many pathological states like, e.g., psoriasis, cutaneous tumours of various nature and several types of alopecia.

It is reported in literature that antioxidant agents and immunostimulants are individually capable of reducing and/or eliminating all reactions intervening to cause the oxidative stress, first of all the formation of lipid peroxides.

Melatonin

Melatonin, though carrying out antioxidant activity, is commonly used merely for the induction it performs towards sleep/wake threshold (Brziezinski A (1997) N. Engl J. Med 336: 186-195). According to previous studies, melatonin has been associated with vitamins C and E, and it has been observed that this association develops an antioxidant activity superior than the sole use of melatonin itself (Dreher F, Gabord B, Schwindt D H, Maibach H I (1998) Br. J. Dermatol 139: 332-339).

Carotenoids

The antioxidant activity of carotenoids is described in literature (Foote C S, Chang Y E, Denny R W (1970) J. Am. Chem. Soc. 92: 5218-5219; Hill T J, Land E J, McGarvey D J; Schalch W et al (1995) J. Am. Chem. Soc. 117: 8322-8326).

Moreover, it has been demonstrated how vitamin E (lipophylic) is capable of repairing the carotene-radical created by oxidation inside the cell membrane, whereas vitamin C (hydrophilic) present inside the extracellular space in turn neutralizes Vitamin E radical, in turn oxidizing into dehydroascorbic acid outside the cell membrane (Bohm F, Edge R, Land E J et al (1997) J. Am. Chem. Soc. 119: 621-622).

Alpha-lipoic Acid

The antioxidant action of alpha-lipoic acid is described in literature by Pelle et al. (1999) Photoderm. Photoim. 15: 115-119.

Immunostimulants

Among immunostimulants, it is widespread the use above all of beta-glucan and carboxymethyl betaglucan for its immunostimulant abilities, demonstrated both in the topical and systemic use thereof. (Stone B A, Bohnn J A, Miller J N (1995) Carbohydrate Polymers 28:3-14; Luzio N R (1987) TIPS 344-347).

Since the specific mechanism of cellular death by oxidative stress has not been fully elucidated, there is an increasing commitment in setting cosmetic/therapeutic strategies apt to prevent cellular damage deriving from oxidative processes. Though each of the above compounds is already promising as a protective agent, both for skin and cutaneous annexes, there remains the need of novel and more active compounds, or of an improved use thereof, so that they be more effective both in the short and in the long run.

Summary of the Invention

In progress works carried out by the present inventors have demonstrated on in vitro cellular models how antioxidant administration carries out a cytoprotective action towards aggression by free radicals of Oxygen (reactive oxygen species) (ROS). This action was observed in particular with melatonin, but also with associations of melatonin and other active substances, which at suitable concentrations are capable of preserving cell vitality on an in vitro model. However, the same works have highlighted that under increasing concentrations of melatonin or other antioxidants, cell vitality tends to reduce. In particular it was observed, with a preliminary investigation carried out on cultures of nerve cells taken as experimental model, that antioxidant concentrations have to be carefully evaluated a priori to avoid any toxic effect.

These observations suggest that an increased effectiveness in oxidative stress prevention and treatment cannot be attained merely by using high concentrations of a single antioxidant substance, but solely by identifying novel associations of substances capable of developing a synergistic effect even at a low concentration.

Therefore, object of the present invention is a mixture of substance comprising melatonin and at least one additional substance selected from immunostimulating substances and antioxidant substances.

In particular, object of the invention is a mixture comprising melatonin, at least one immunostimulant substance and at least one antioxidant substance.

A second object of the invention are the above-mentioned mixtures of substances for cosmetic use in the treatment of the aging and photo-aging of tissues and cutaneous annexes.

A third object of the invention are cosmetic compositions comprising, as active principle, an association of substances according to the invention, an excipient and pharmaceutically acceptable adjuvants and additives.

Further objects of the invention are a method of preparing the compositions of the invention and uses of the same combinations.

DETAILED DESCRIPTION OF THE INVENTION

Figure 1:
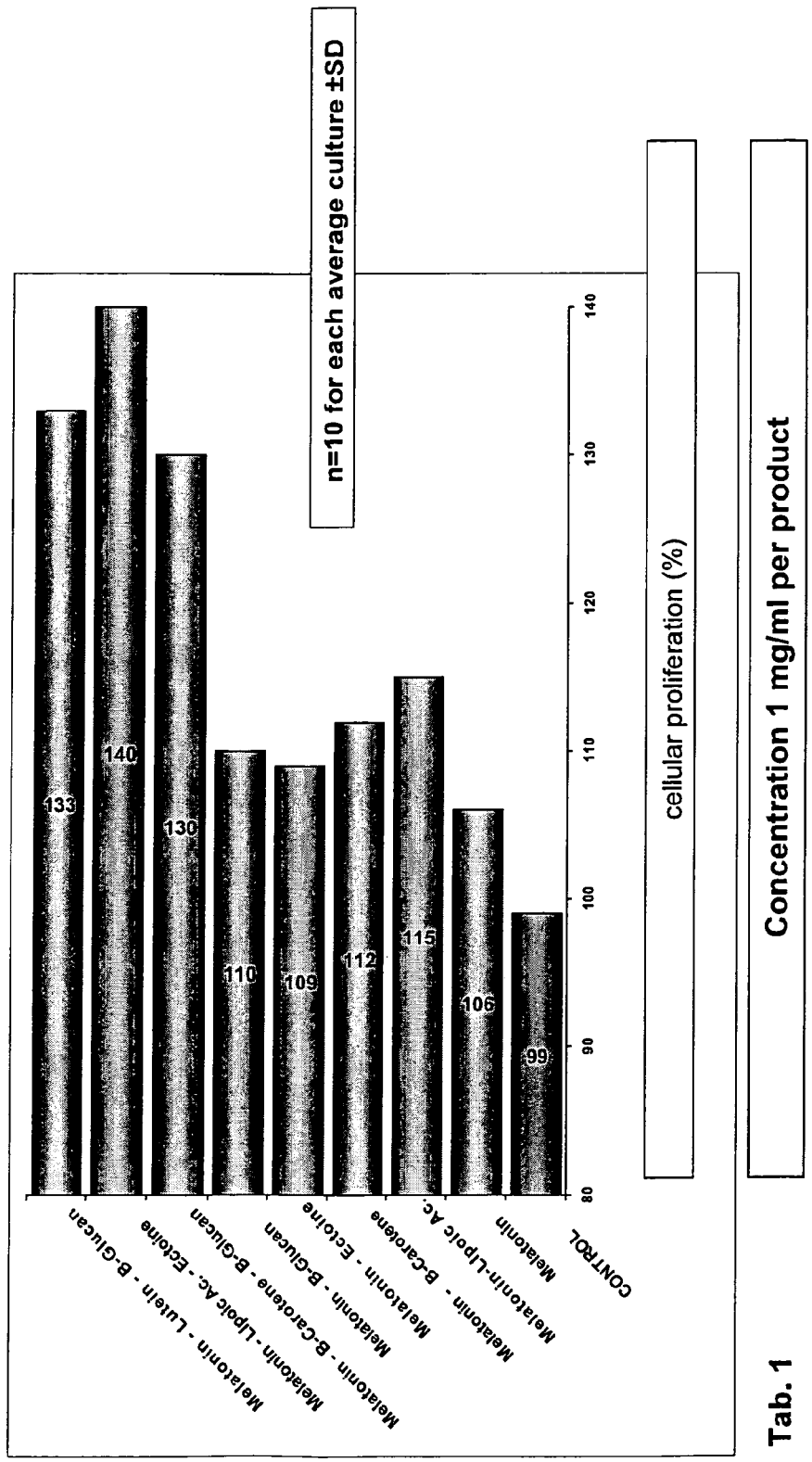
FIG. 1 illustrates the percent values of fibroblast growth stimulated by melatonin in a mixture with antioxidants and immunomodulants.
Figure 2:
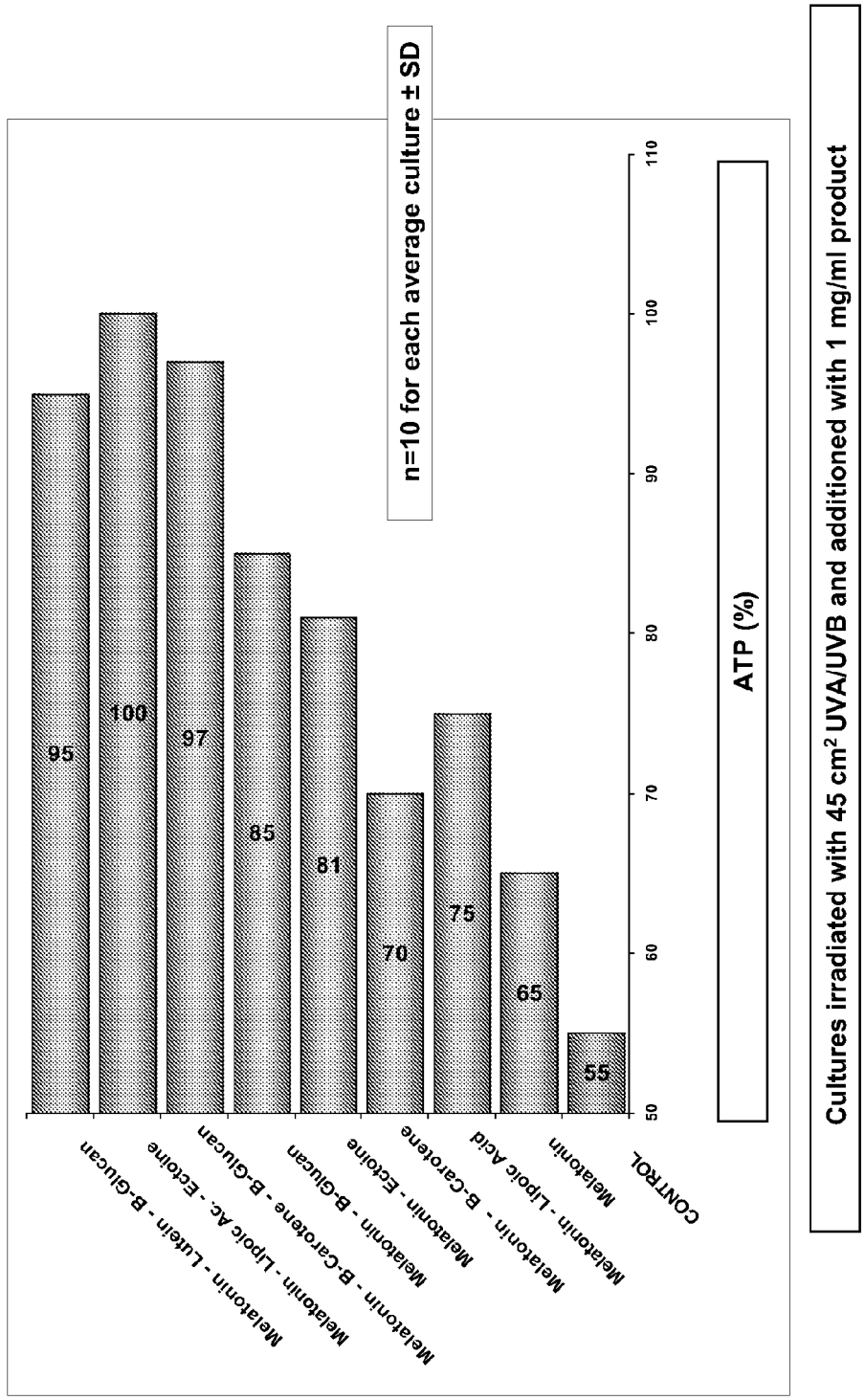
FIG. 2 illustrates ATP protection from UVA/UVB irradiation.
Figure 3:
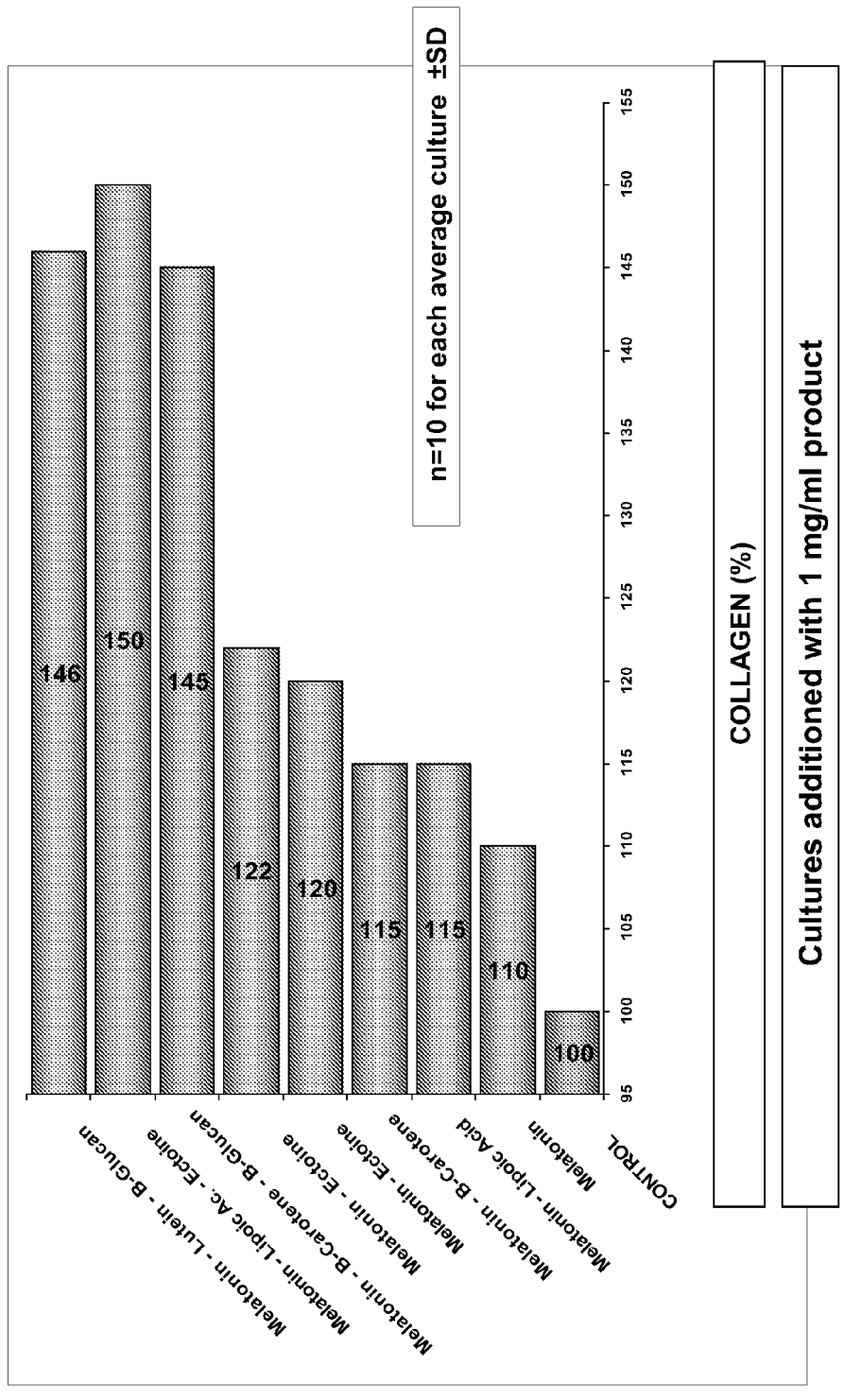
FIG. 3 illustrates the increase in collagen production on fibroblast cultures.
Figure 4:
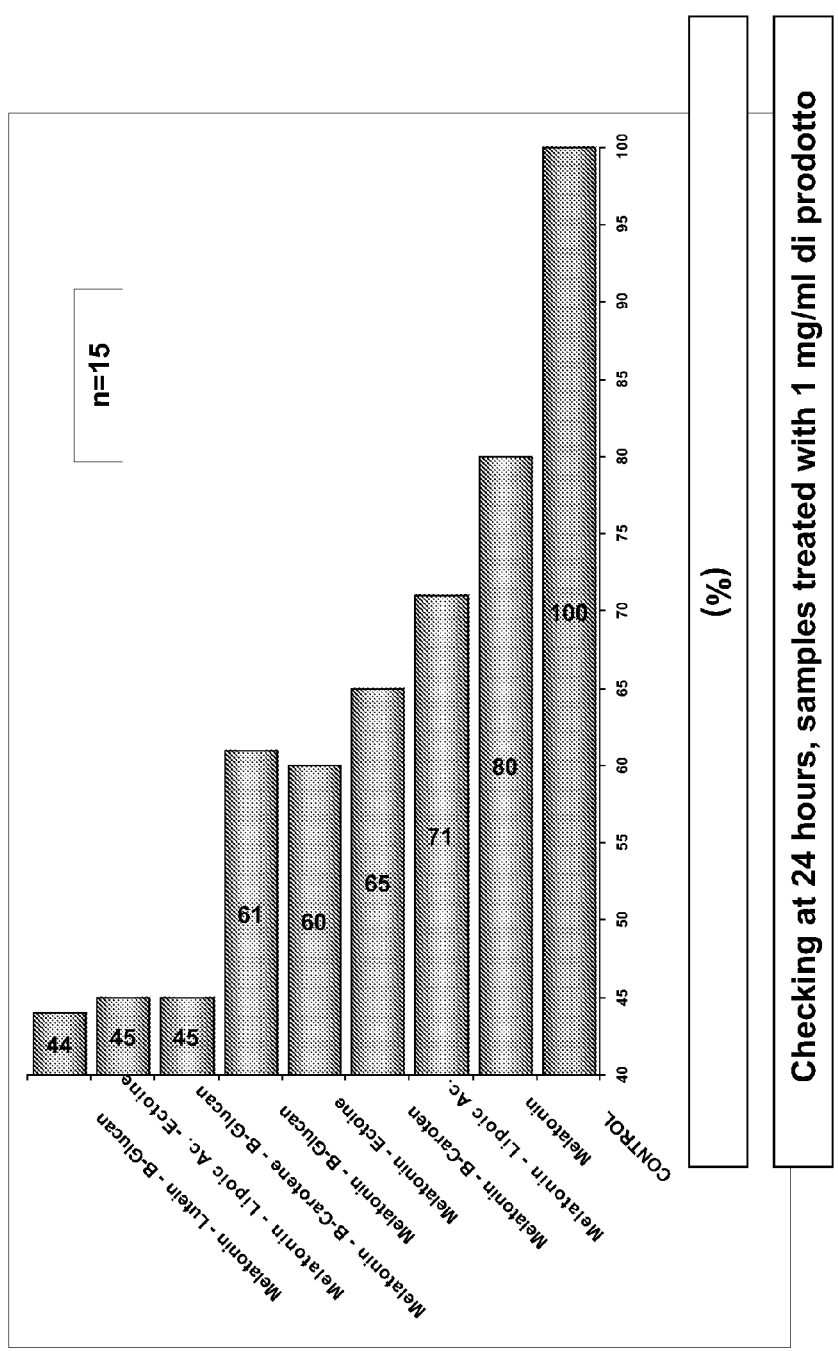
FIG. 4 illustrates IL-8 checking on lymphocytes from volunteers' blood pre-treated with antioxidants and immunomodulants.
Figure 5:
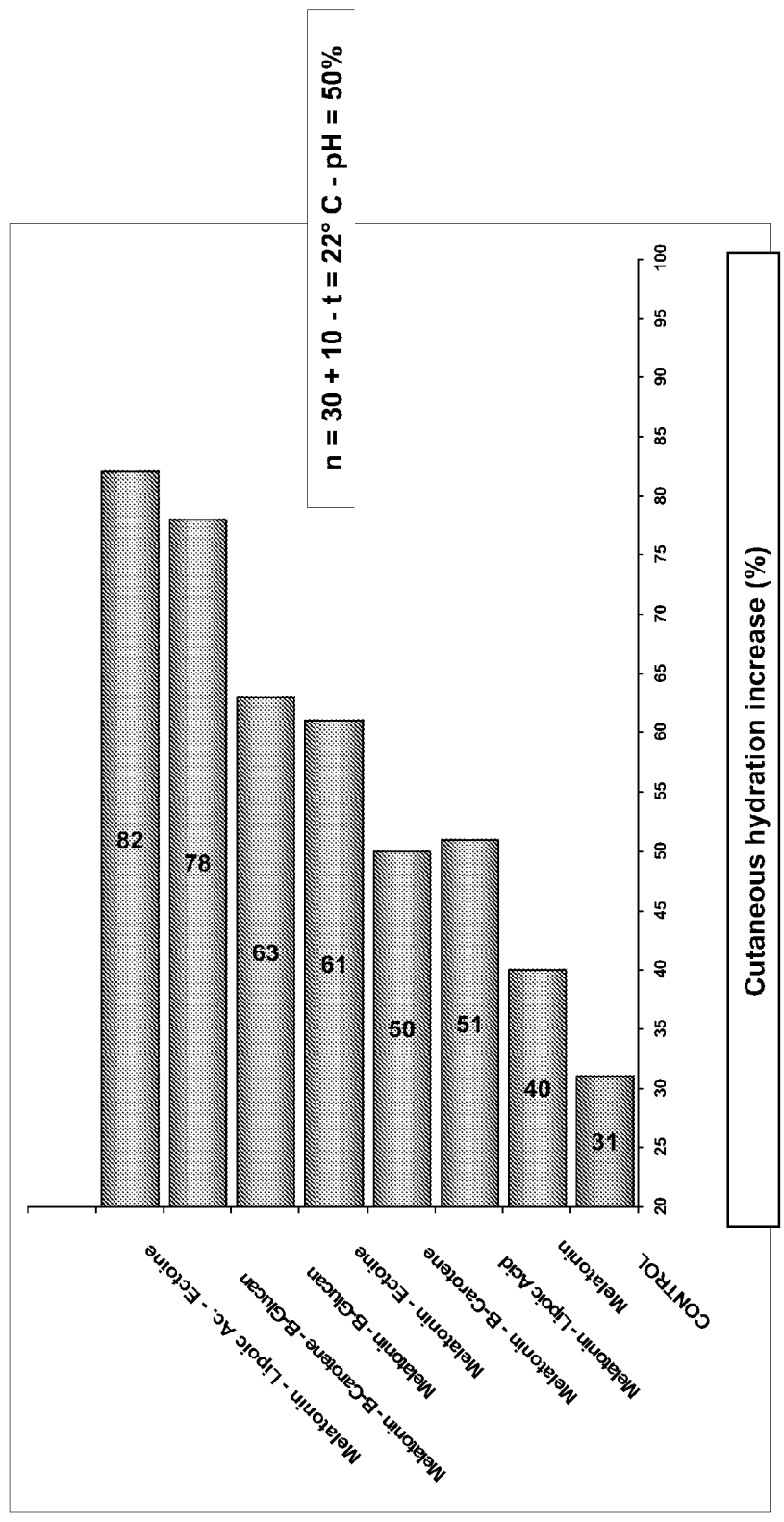
FIG. 5 illustrates the checking of cutaneous hydration of persons suffering from cutaneous dryness after 60 days of bi-daily treatment on face skin.
Figure 6:
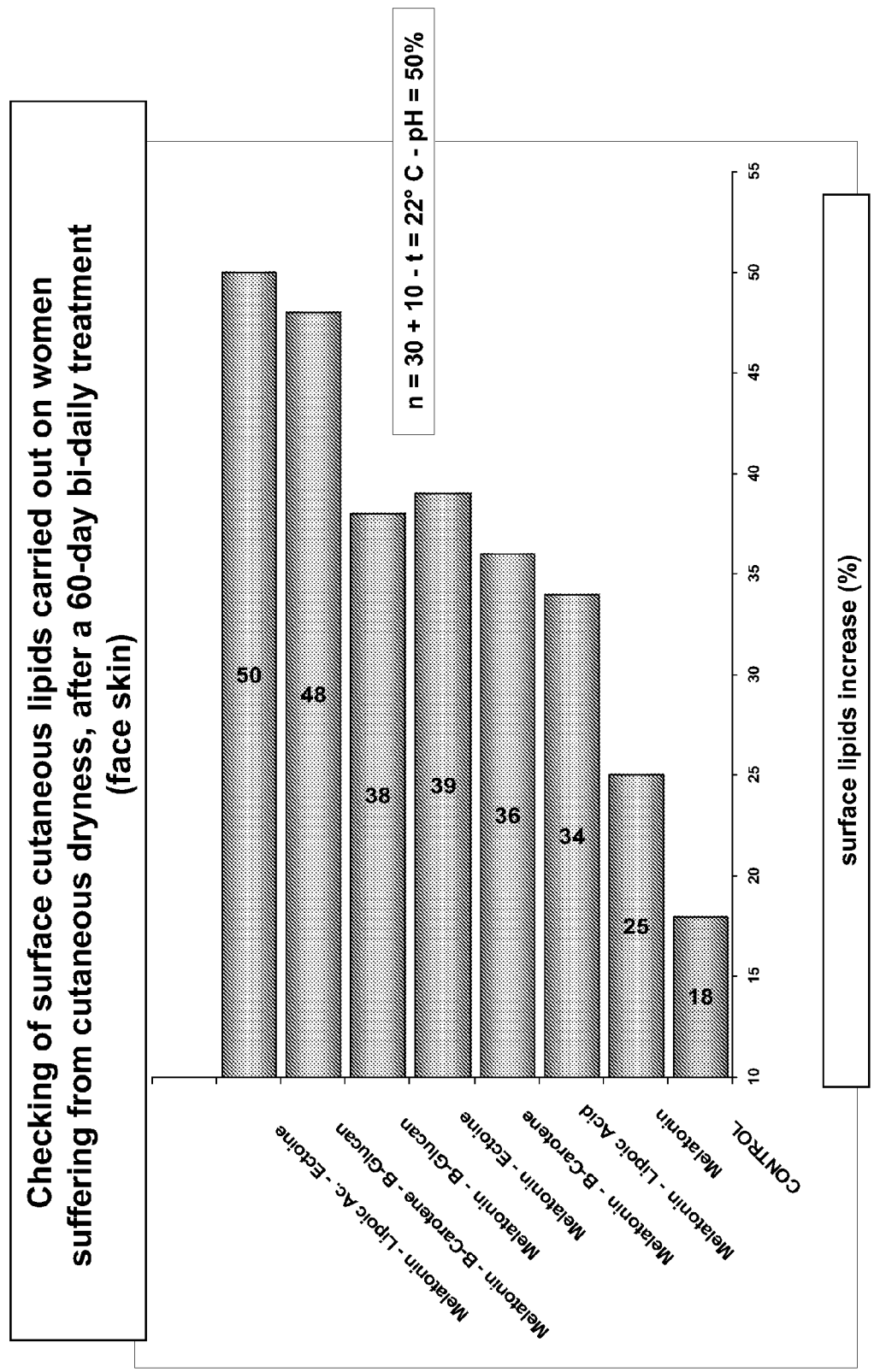
FIG. 6 illustrates skin surface lipids checking carried out on women suffering from cutaneous dryness, after 60 days of bi-daily treatment (face skin).
Figure 7:
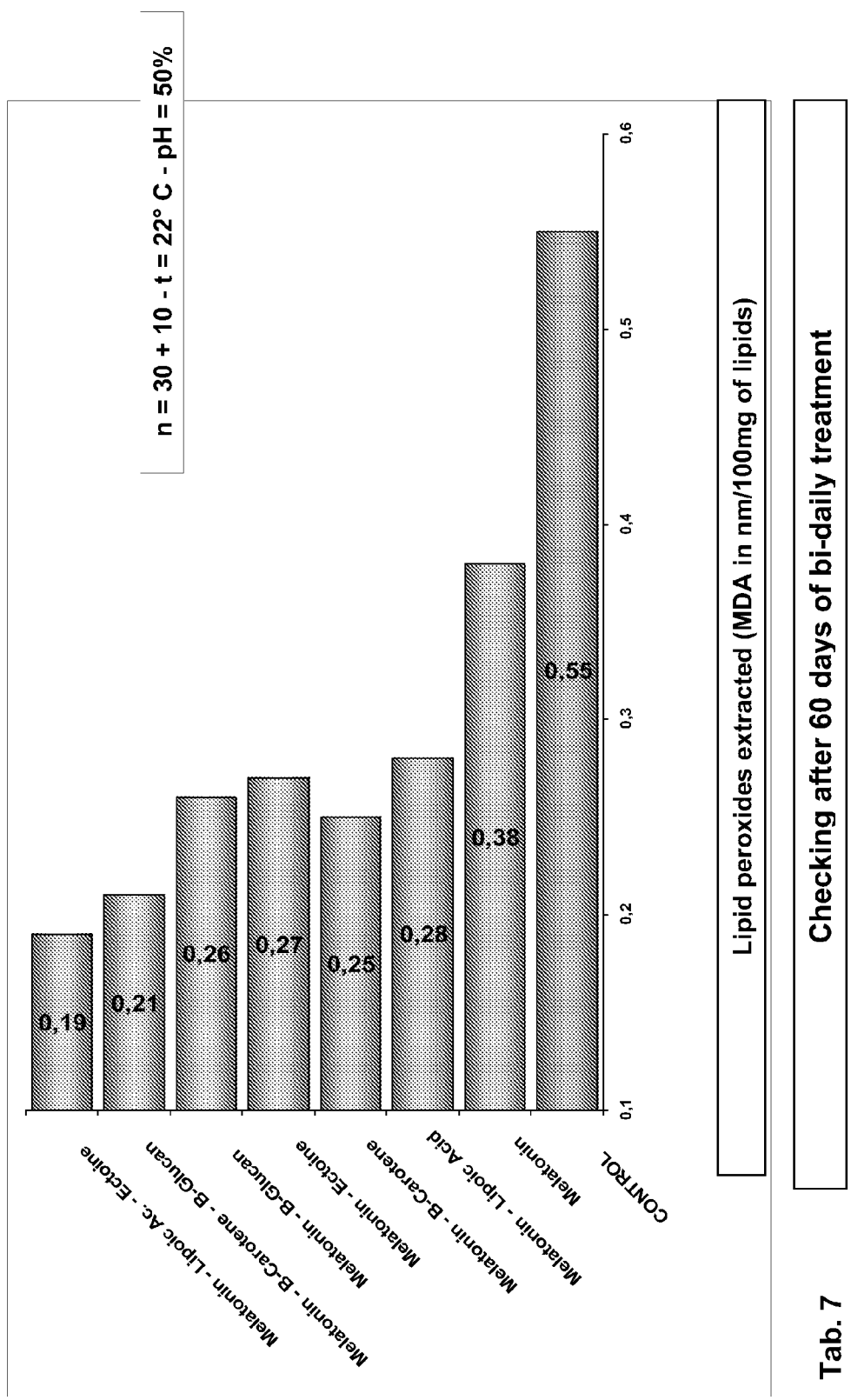
FIG. 7 illustrates the concentration of lipid peroxides found on arm skin of women suffering from dryness (average of 3 assessments).
Figure 8:
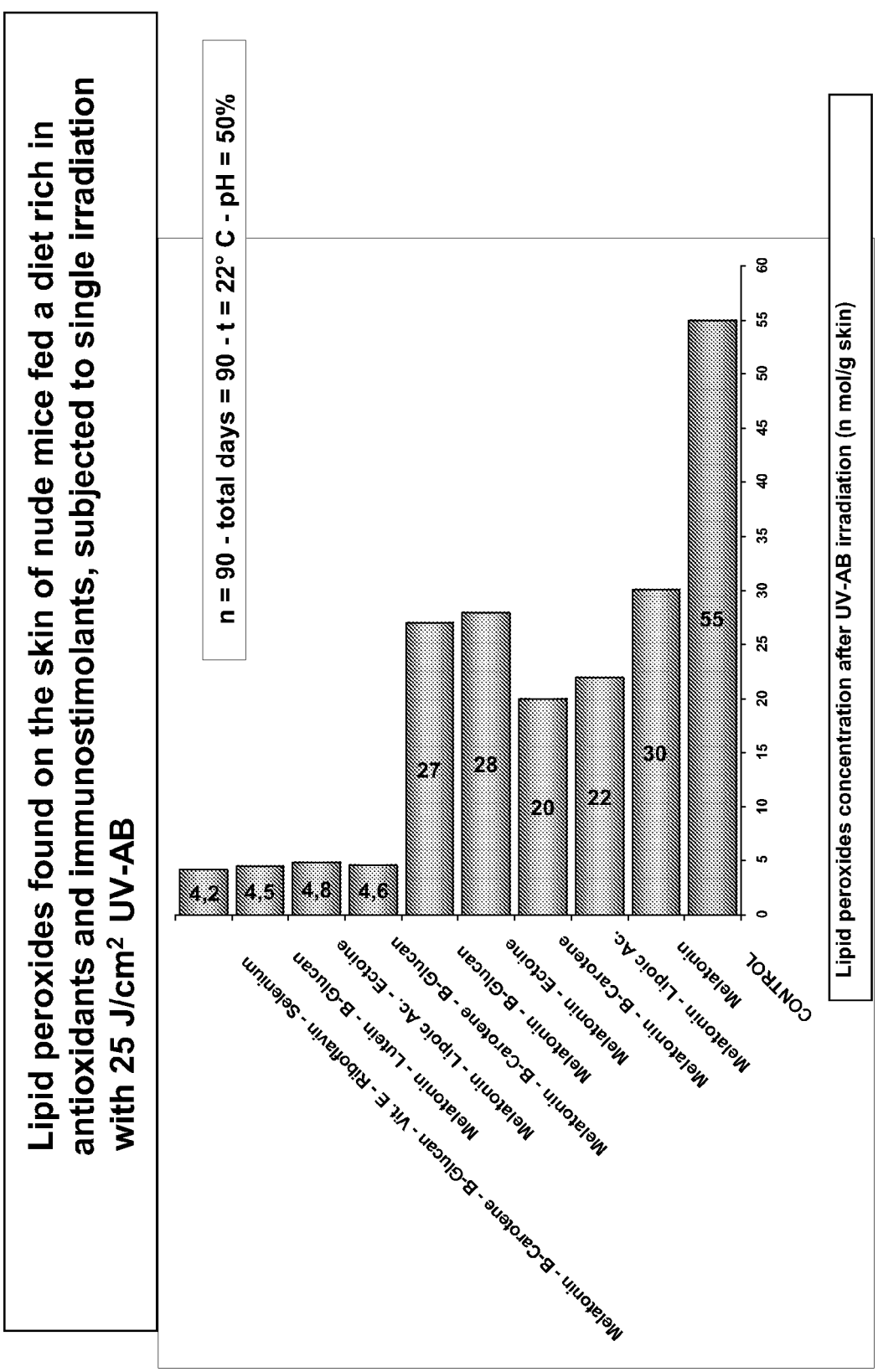
FIG. 8 illustrates the concentration of lipid peroxides found on the skin of nude mice fed a diet rich in antioxidants and immunostimulants, subjected to single irradiation with 25 J/cm$^2$ UV-AB.
Figure 9:
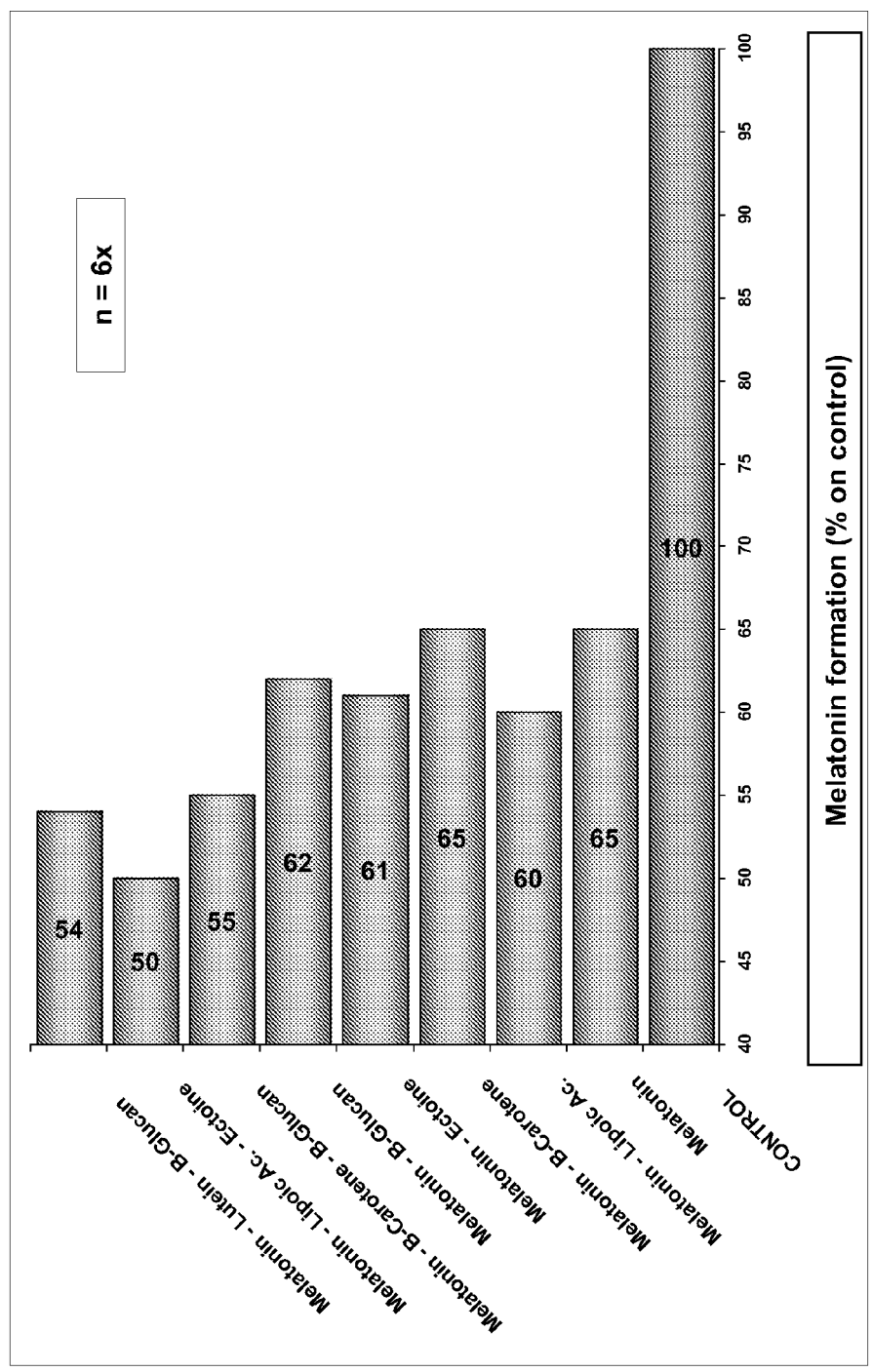
FIG. 9 illustrates the depigmenting activity carried out by different mixtures of antioxidants and immunomodulants on (R16) melanocyte growth.
Figure 10:
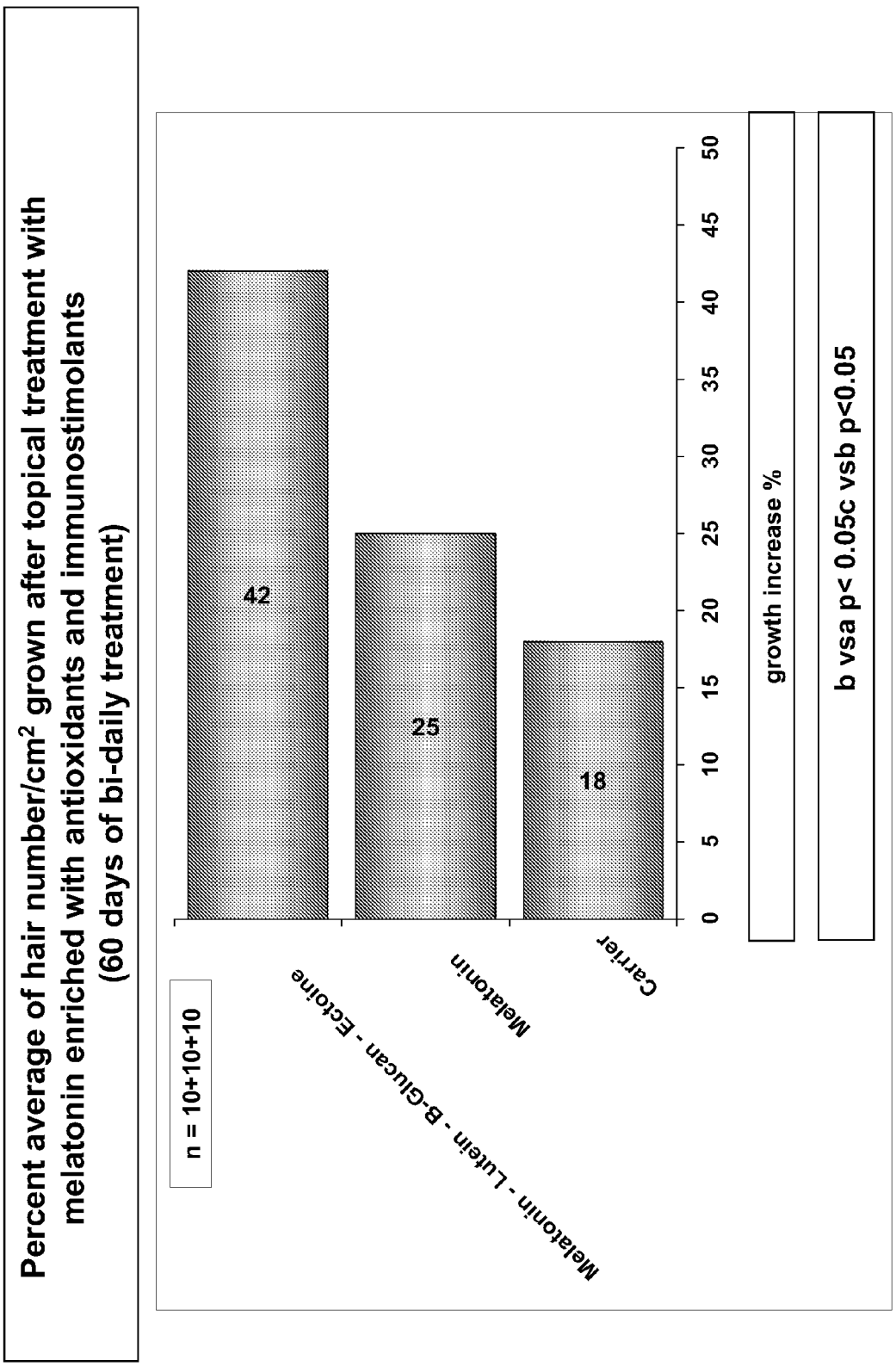
FIG. 10 reports the percent average of number of hair/cm$^2$ grown back after topical treatment with melatonin enriched with antioxidants and immunostimulants (60 days of bi-daily treatment).
Figure 11:
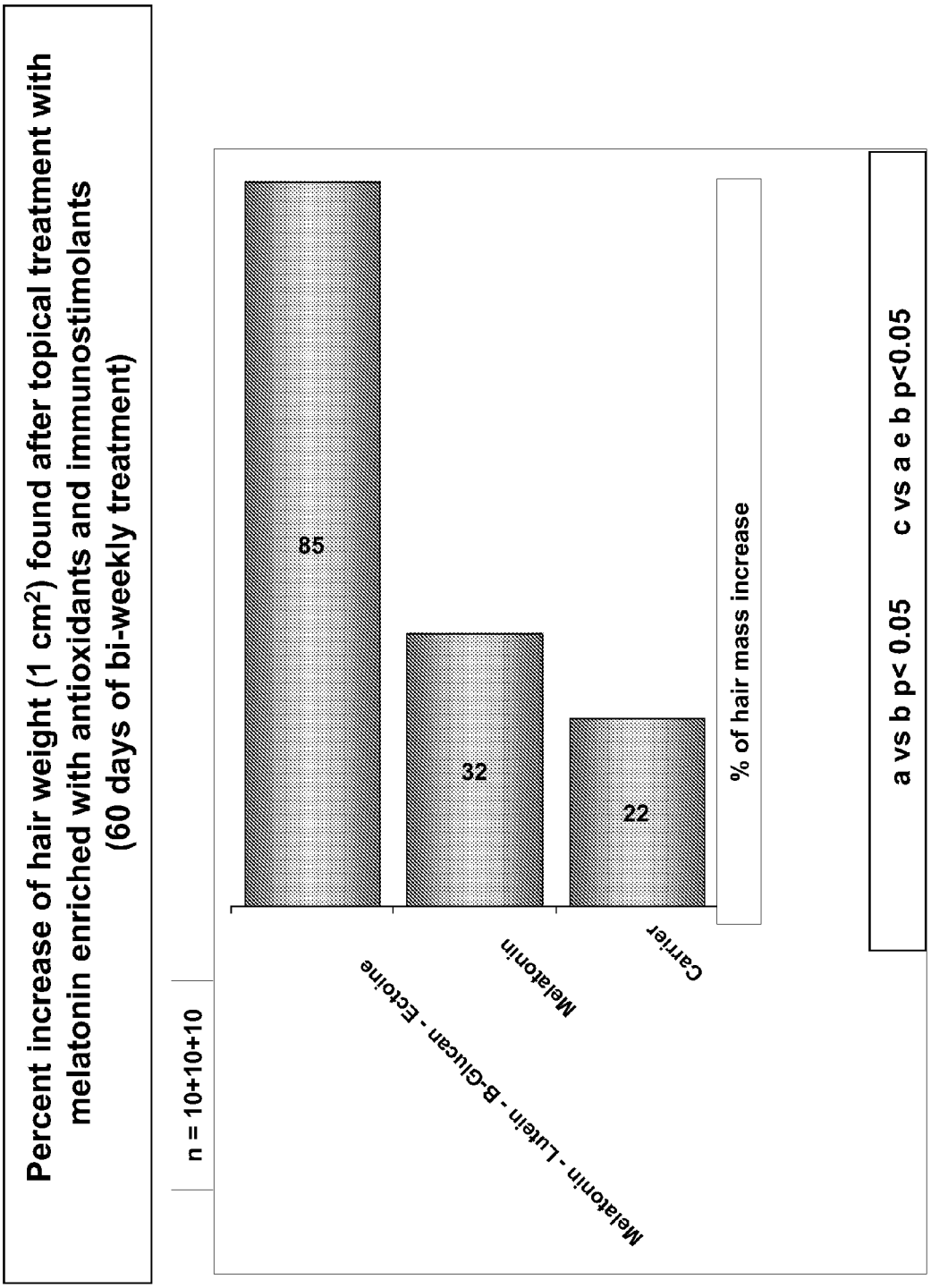
FIG. 11 reports the percent increase of hair weight (1 cm$^2$) found after topical treatment with melatonin enriched with antioxidants and immunostimulants (60 days of bi-weekly treatment).

The invention is based on the use of associations of antioxidant substances comprising melatonin as antioxidant of choice and supplementing (integrating) melatonin's antiradical activity with the activity of other antioxidant and/or immunostimulant substances.

The activity carried out by melatonin is aimed above all at neutralizing of hydroxyl radicals (OH$^-$.) though it is capable of neutralizing also the singlet oxygen. It is interesting to point out how this highly lipophilic molecule is capable of easily penetrating through the cell membrane, reaching all cell sites.

Melatonin activity may be modulated and strengthened by other antioxidant substances, which potentiate its anti-aging and anti-photoaging activity, remarkably reducing free radical formation and thereby improving the aspect both of skin and hair.

Antioxidant substances are selected from carotenoids, water-soluble antioxidants like lipoic acid and vitamin C, and lipid-soluble antioxidants like vitamins E, A or their mixtures. Preferred antioxidant mixtures are β-carotene, lutein and/or lipoic acid, with or without the presence of vitamins E, A and C and derivatives thereof and of the coenzyme Q10.

Carotenoids are highly lipophylic molecules, acting by neutralizing the singlet oxygen radical ($O_2^-$.) though being very reactive also towards peroxyl radicals (OH$^+$.). Any type of carotenoid is useful in the associations of the invention, e.g. Beta-carotene, lutein, zeaxanthin, lycopene, proanthocyanins, flavonoids and other polyphenols obtainable even from vegetable juices, like apple, raspberry, pink orange, hawthorn juices, etc.

Alpha-lipoic acid is it also a powerful natural antioxidant, capable of neutralizing and eliminating both the ROS and the NOS, also thanks to its double solubility in lipids and in water. In fact, its amphiphilic characteristics allow it to carry out the antioxidant action both inside the cell, at the mitochondrial level, and outside it, in extracellular spaces.

Lastly, an essential component of the mixtures of substances of the invention are immunomodulating/immunostimulating substances, which by potentiating the organic defences of the organism interact with the direct action of the antioxidants, stimulating their activity with synergistic effects as demonstrated in the experimental section. Preferred immunomodulant/immunostimulant substances are in particular ectoine, β-glucan and carboxymethyl betaglucan, Zinc pirithion (for topical use) and the oral derivatives of zinc, like, e.g., lactate, gluconate and picolinate; amino-sugars, like, e.g., glucosamine and in particular N-butyl-glucosamine and its homologues; carnitine and its derivatives (Bagchi D, Bagchi M, Stohs S J et al. (2000) Toxicology 148: 187-197; Reiter R J (1998) Nutrition 14: 691-696.).

Preferred associations are binary associations comprising, e.g.: melatonin and lipoic acid; melatonin and beta-carotene; melatonin and ectoine; melatonin and beta-glucan, or ternary associations containing melatonin, beta-glucan and beta-carotene; melatonin, ectoine and lipoic acid; melatonin, lutein and beta-glucan. In any association, any single constituent may be replaced by two or more substances of the same type, e.g., beta-glucan may be replaced by, or supplemented with carboxymethyl betaglucan. In general, an association may concomitantly contain lutein, lipoic acid and/or beta-carotene, as well as ectoines, beta-glucan and/or carboxymethyl betaglucan. E.g., associations containing melatonin, lutein, beta-glucan and ectoine may advantageously be used.

Moreover, in all these associations lipoic acid may be replaced by or supplemented with vitamins, like vitamins A, C, E, tocotrienols and their derivatives, and the coenzyme Q10.

The associations of the invention are formulated in compositions suitable for cosmetic or therapeutic use for topical or systemic application, in particular for on-skin application or transcutaneous, intradermal or subcutaneous administration. Compositions for topical use are in the form of solution, lotion, cream, emulsion, gel, spray, foams, film, each of which may be applied directly on-skin or on cutaneous annexes. Alternatively, the associations of the invention in the above formulations may be adsorbed on supports such as fabrics, face masks, plasters, synthetic supports and other means for on-skin application. Likewise, compositions for oral use will be solutions, emulsions or solid compositions, like tablets, soft or hard capsules, or powders or lyophilised granulates.

Compositions for intradermal or subcutaneous use may be distilled water solutions or physiological solutions with or without buffer addition.

Emulsions may be O/W (Oil/Water) or W/O, or W/O/W and O/W/O, better when micro- or nanoemulsions, but may also be dispersions or colloidal solutions. Microemulsions may be proposed as gels, creams, mechanical-gaseous sprays, given also in the form of foams. For the preparing of the emulsions there may be used all known surfactants, with a preference for the silicone, glucoside and phospholipid ones. Since the cutaneous barrier hinders the transit of any hydro- and liposoluble substance, means capable of facilitating the transcutaneous penetration is extremely interesting, both pharmaceutically and cosmetically, within the scope of the present invention. For instance, it has been observed that chitin nanofibrils of average dimensions of about 240 nm are capable of penetrating easily the cutaneous layers, carrying substances of small or medium molecular size, like, e.g., melatonin, lutein among antioxidants, or ectoine among immunomodulants. Therefore, in an alternative embodiment the component substances of the mixtures of the invention may be adsorbed or linked by ionic bonds to chitin nanofibrils in order to foster their transcutaneous penetration and to increase their bioavailability. Chitin nanofibrils useful therefor are described in literature (WO-A-2006/048829).

In accordance with the invention, melatonin is used in dosages ranging from 0.005 mg to 10 mg per dosage unit, per os, or by unitary amount of topical application, preferably from 0.005 mg to 1 mg by topical application, and from 1 to 6 mg by oral administration.

The ratio between melatonin and any other single component of the association may range from 1:0.005 to 1:1, up to 1:50 for each single component used alone or in association with others of the same type.

Vitamins may be added in concentrations ranging from 5 to 100 mg per dosage unit or fraction thereof and used individually and/or in mixture.

Generally valid weight ratios among melatonin, immunostimulant and antioxidant are: for 1 mg melatonin, from 0.005 mg to 50 mg immunostimulant and from 0.005 mg to 50 mg antioxidant.

Examples of preferred weight ratios among components of the mixtures of substances (melatonin/β-carotene/β-glucan/E vitamin) for topical use are, respectively: 0.5 mg/0.005 mg/0.5 mg/0.5 mg, whereas orally they are, respectively: 5 mg/7.5 mg/10 mg/10 mg.

Subcutaneously or intradermally, the preferred ratio is: 0.5 (melatonin): 0.05 (immunostimulant): 0.05 (antioxidant): 0.5 (water-soluble vitamins) where beta-carotene may be replaced with lipoic acid, whereas vitamin E may be replaced by vitamin C and its derivatives, and/or other water-soluble vitamins.

The strong antioxidant action attained with the mixtures of the invention is capable of reducing ROS presence, both at an internal level (blood serum) and at a topical cutaneous level. Free-radical reduction is also accompanied by an increase in cutaneous hydration and elasticity, modulation of the surface lipid film and reduction of cutaneous roughness, also accompanied by a decrease of the so-called age spots and an improvement of the anagen/catagen ratio in the hair growth cycle. In fact, the use of these mixtures is also capable of modulating hair's anagen phase of when it is reduced owing to pathologic forms, such as the various forms of alopecia, or reduced or discontinuous, in the case of a decrease in hair mass and number linked to stress or different environmental factors.

As highlighted from tables 1-9, all of the antioxidants used are particularly effective in protecting cells from damages caused by free radicals, thereby improving their proliferation. In particular, lipoic acid and carotenoids (beta-carotene and lutein) further enhance the positive effects of melatonin. In the tests described hereinafter, lipoic acid is tendentially more active than carotenoids. Analogously, yet probably with different mechanisms, immunostimulants also enhance melatonin action. Under our experimental conditions, The immunostimulant beta-glucan seems to be tendentially more active than ectoine.

Thus, from a careful examination of the results obtained it was verified that, concentrations being equal, the antioxidants, lipoic acid and the carotenoids, and the immunostimulants, beta-glucan, carboxymethyl betaglucan and ectoine, seem to carry out analogous activity as synergizing agents of melatonin's antioxidant action. In fact, it has been observed that, concentrations being equal, both the antioxidants and the immunostimulants, used individually in binary associations with melatonin, produce synergistic effects that comparably potentiate melatonin action.

Lastly, the results observed and reported in the tables demonstrate that the ternary associations of melatonin, an immunostimulant and an antioxidant, further and markedly increase the synergistic effect yielded, though at a low concentration of the single components.

Thus, the activity carried out, e.g., by 3 mg melatonin proves to be significantly lower than the analogous activity carried out by 1 mg melatonin, 1 mg immunostimulant (ectoine or Beta-glucan) and 1 mg antioxidants (betacarotene, lutein, lipoic acid, vitamins C, E and A, and coenzyme Q10), respectively. Just in the light of these surprising results, a study was conducted in order to verify the influence of the mixtures of substances according to the invention on the hair cycle. In fact, significantly influencing hair growth phases constitutes a particularly difficult challenge.

Therefore, it could be demonstrated how the associations of the invention are also capable of exerting a surprising synergistic effect of boosting the anagen phase of the hair growth cycle.

Lastly, it was verified, by a preliminary investigation carried out on nerve cell cultures taken as experimental model, that antioxidants' concentrations should be carefully evaluated a priori to avoid toxic effects. Undergoing studies carried out by the present inventors have demonstrated how toxicity is directly proportional to the concentration of the single active substances taken unitarily, whereas it increases much more slowly when the same end effect sought is attained with low concentrations of plural components. In practice, a single 3-mg dosage of melatonin alone proves far more toxic than the dosage of an association of melatonin, carotenoid, immunostimulant, each in an 11-mg amount.

Experimental Section

In Vitro Activity

On Fibroblasts

As it is known, dermis represents the fundamental and supporting portion of skin. The papillary portion of dermis contains a high amount of collagen and elastic fibres required to give firmness and elasticity to the skin. Fibroblasts, contained in high amounts in the papillary derma, are appointed to the continuous production of these fibres. Cutaneous aging causes a thinning of the derma and a qualitative and quantitative reduction of the fibroblasts, not anymore capable of efficiently producing the fibres. Thus, it was checked the effect exerted by melatonin on the growth of a fibroblast culture used alone and in association with antioxidants and immunostimulants.

Method

Fibroblasts of NB1RGB strain were used ($2\times10^5$ cell/ml) and suspended in the α-MEM culture medium placed in 10 Petri dishes (containing 10% foetal bovine serum (FBS), 100 units/ml penicillin and 100 g/ml streptomycin).

To the various cultures there were added, respectively:
(1) melatonin;
(2) melatonin/lipoic acid;
(3) melatonin-β-carotene;
(4) melatonin-ectoine;
(5) melatonin-β-glucan;
(6) melatonin-β-carotene-β-glucan;
(7) melatonin-lipoic acid-ectoine;
(8) melatonin-lutein-β-glucan,
while two were left as control. All products were additioned in a 1 µg/ml concentration.

The results obtained are reported in Table 1 (FIG. 1), illustrating the cell proliferation percent with respect to the control value.

Regenerative Activity

Skin regeneration process is very efficient in young people and in healthy skin, drastically reducing with aging. External influences such as stress, loss of sleep, air conditioning, reduce the normal cellular turnover.

Also this phenomenon contributes to the general aging of skin, and it may be checked with different methods, e.g. by assessing the energy required for the various metabolic processes, stored as ATP.

Control of the ATPasic Activity

All biochemical processes require energy that is accumulated in the form of ATP (adenosyn-triphosphate). Therefore, ATP was checked on a culture of keratinocytes irradiated with $4J/cm^2$ UVA+04 $J/cm^2$ UVB and in comparison with keratinocytes irradiated and additioned with the products under study. Of course, irradiation causes a drastic reduction in the ATP present.

Out of the 9 culture-containing Petri dishes used, 8 were additioned with 1% µg/ml of the different substances to be tested, whereas one served as control.

Results are reported in table 2, illustrating the residual percent amount of ATP per dish.

Stimulation of Collagen Synthesis

A continuous and regular collagen synthesis is of fundamental importance for the ECM (extracellular matrix) structure, and therefore for skin elasticity and compactness and wrinkle reduction. Collagen 1 presence was verified with the use of specific antibodies on all ten cell cultures, 8 of which enriched with 1% µl/ml of the various substances directly introduced in the culture medium, and one as control.

Results are reported in table 3, illustrating the percent increase of collagen with respect to the control value.

In Vivo Activity

IL-8 Control

External aggressions give rise to an immune response, always accompanied by inflammatory reactions. When these reactions are abnormal, an abnormal cascade and related production of pro-inflammatory mediators are reached.

Interleukin 8 (IL-8) is the most accountable for the permanence of the inflammatory state (Zheng M, Sun G, Mrowietz U. (1996) *Exp dermatol* 5(6) 334-340).

Experimental Protocol 10 volunteers suffering from cutaneous dryness of atopic origin and of age ranging from 15 to 20 years were selected.

Collected blood aliquots, pre-supplemented and non-supplemented with the components under study (1 µl/ml) were subdivided into 10 Petri dishes, 8 of which were further supplemented with 10 µl/ml Tumor Necrose Factor a (TNF-α), and one left as control. TNF-α addition caused a marked increase in IL-8 production, whereas the substances or associations of the invention reduced said increase. IL-8 amounts were determined photometrically, by specific antibodies.

The results obtained are reported in table 4, illustrating the relative amounts of freed IL-8 with respect to the control value.

Hydroperoxide Control

Skin surface lipids are sensitive to attacks by oxygen present in the environment and/or caused by endogenous processes giving rise to formation of lipid peroxides.

These compounds may be neutralized or prevented in their formation by use of cosmetics and/or food supplements carrying out antioxidant activity.

Influence of the Substances Under Study on Skin Characteristics

Experimental Protocol

To a group of 30 women volunteer of age ranging from 25 to 35 years, suffering from dry skin, there were distributed under double-blind conditions two different typologies of creams to be applied by light massage on the left arm and on the right arm, in the morning and in the evening, respectively, and on the two hemi-areas of the face.

The two creams, contained in differently-colored tubes, sufficed for 60 days of treatment. Other 10 women were given the control product (carrier alone) and the product labelled with number 1 (melatonin).

At the checking, carried out at +60 days, the treatment groups were subdivided as follows:

GROUP 1 (30 women):
10 women treated with products 2 (melatonin and lipoic acid) and 3 (melatonin and beta-carotene),
10 women treated with products 4 (melatonin and ectoine) and 5 (melatonin and betaglucan),
10 women treated with products 6 (melatonin, betacarotene and betaglucan) and 7 (melatonin, lipoic acid and ectoine);

GROUP 2 (10 women) treated with the control and with product 1 (melatonin).

During the checking, skin surface lipids and hydration were verified by 3C System.

The results obtained are reported in tables 5 and 6, which illustrate the percent increase of skin hydration, and of skin lipids with respect to a theoretical reference value, respectively.

Lipid Peroxides

Lipid peroxides were checked with the Pugliesi method (Pugliesi P. (1990) Assessment of Antiaging Products. In: W.C. Wagguner Clinical Safety and Efficacy Testing in Cosmetics, Marcel Dekker Inc., NY, PP 306-309) determining the presence of these derivatives by malonyl dialdehyide (MDA) use.

The results obtained are reported in table 7, illustrating the diminution of the values of lipid peroxides found on skin.

Lipid Peroxides on Nude Mice 100 naked mice (HRS/J) were subjected to the treatment, subdivided into 10 groups of 10 individuals each, fed standard mice diets additioned beforehand with 0.8 mg/Kg of the various mixtures of antioxidants and immunostimulants denoted by numbers 1 to 9, beside the control. This experiment was meant to assess the protective activity of these compounds if and when taken orally.

Mice who had regularly taken the diet for 60 days were irradiated, under anaesthesia, only once with 25 J/cm$^2$ (about 10MED).

Right after irradiation, skin was removed from the irradiated lateral zone and the non-irradiated contralateral zone. Post-extraction with examination, the residue brought to a dry state was redissolved into methanol/ethanol (1:1). HPLC-separated lipid peroxides were measured by chemoluminescence. (Jamamoto Y, Brodsky M H, Baker J C and Ames B N (1987) *Anal. Bioch.* 160.7-13)

The results obtained are reported in table 8, illustrating the post-irradiation concentration of lipid peroxides. The protective effect exerted by the associations of substances of the invention is evident.

In Vitro Depigmenting Activity (Age Spots)

Any depigmenting activity of the mixtures of products was verified on B16 melanoma cells (5×10 cell/ml) suspended in MEM culture medium (10% FBS, 1000 I.U. (International Units)/ml penicillin and 100 µg/mg streptomycin) containing 2 mM teophylline. The suspension was subdivided into 7 500-µl portions. To each portion, placed in suitable bars, 50 µl/ml of the various mixtures of active agents were added. Of each mixture 6 samples were prepared.

Post-incubation, 300 µl PBS were added, then all samples were ultrasonicated. Higher or lower presence of melanin was checked by 415-nm spectrophotometer. The associations of the invention cause significant decrease in melanin formation.

The average results obtained are reported in Table 9, illustrating percent values with respect to the control value.

Action on the Anagen Phase of Hair Cycle

Hair fibre is produced during the anagen phase, to the extent of about 1 cm/month, or 0.35 mm/day, and expelled during the telogen phase. The anagen phase generally lasts from 2 to 6 years, the telogen one 3 months and the intermediate catagen one 3 weeks. This cycle is generally analogous for all scalp area. Owing to reasons linked to actual pathologies or environmental causes, or to a way of life subjected to too many frequent stresses, an alteration of this cycle may occur, with loss of hair, which thereby are reduced in number and thickness.

Given our previous experiences (Morganti P, Fabrizi G, James B and Bruno C. (1998) *J. Applied Cosmetol.* 16: 57-64) we wanted to check whether the activity carried out by a solution of active principles (capillary lotion) already partly used could be enhanced or improved by use of the antioxidants and immunostimulants under study.

The above lotion was deprived of the active constituents of Serenoa Repens, more suitable for forms of androgenetic alopecia. This novel lotion would seem more suitable for all those forms of loss of hair caused by forms of traumatic or chemical alopecia. On the other hand, given the specific activity carried out by the antioxidants and immunostimulants considered, the solution can prove useful to potentiate anyhow the scalp, thereby improving hair glossiness, body and resistance to pulling and traumatic treatments like decolouring, and ironing or perming.

Experimental Protocol

Thirty volunteers (15 women and 15 men) suffering from general hair problems: slight thinning out, thinning, continual loss of hair and occasional formation of forms of alopecia restricted to scalp areas, were subjected to the treatment.

The forms of alopecia, checked by an expert dermatologist, were almost certainly due to forms of psychological-physical stress of the subjects examined and carefully selected in the month preceding the start of the testing.

All subjects were given, under double-blind conditions, a lotion to be applied morning and evening by light friction, in the amount of 5/6 drops poured on the various areas and deemed sufficient for the treatment of the entire scalp.

The 3 lotions were labelled with letters A (base carrier), B (carrier additioned with melatonin), C (carrier additioned with melatonin, β-glucan, ectoine and lutein) respectively.

The study lasted 60 days.

At day 0, an area of about 1 cm$^2$ was delimited in the anteroparietal zone of the scalp, from which hair was carefully removed. Removed hair were weighted to verify the mass thereof, and the number of follicles present was counted by a suitable grid.

At day +60, the number and weight of regrown hair were reassessed, again checking the number of follicles present.

The average results obtained are reported in Tables 10 and 11.

As clearly evident by comparing Tables 10 and 11, melatonin, as it is already known (Fischert, Wigger-Alberm W, Elsner P (1999) Hautarzt 50 (1):5-11) causes an increase of the anagen phase of hair, thereby enhancing its regrowth, without however exerting an effect on the hair weight itself—and therefore on its volume.

On the contrary, the addition of antioxidants and immunostimulants to the solution causes not merely a greater enhancement in hair regrowth, but also influences its volume, and therefore its body.

In fact, all subjects treated with lotion C noticed this phenomenon, and declared themselves very satisfied with the experimental treatment.

Assessment of Cutaneous Absorption of Nanostructured Chitin Associated to Melatonin, Lutein, Ectoine For this purpose, binary mixtures were prepared with equivalent amounts (1:1) of nanofibrils of chitin and of melatonin, or lutein or ectoine.

A known amount (1 mg) of lutein in crystals was dissolved in 50 ml organic solvent (chloroform) and the same amount (1 mg) of chitin nanofibrils was added to the solution. The yielded suspension was kept under mechanical stirring and under sonication for about 2 hours. Then, it was filtered under vacuum with a Buchner filter.

The residual yellow-red-coloured filtrate on the filter, constituted by lutein-bound chitin nanofibrils, was checked under scanning electron microscope (SEM). The remainder of the solution was dried under vacuum, yielding another red crystalline mass, shown to be a mixture of lutein, nanofibrils and lutein-bound nanofibrils. By weight difference, it was observed that from 20 to 30% of the lutein remains bound to the nanofibrils.

The step was repeated by mixing thereamong a mixture containing 2% melatonin or ectoine, both water-soluble, with a 2% chitin nanofibril suspension, attaining a final concentration of 1% for both active agents. Also this suspension was kept under mechanical stirring and under sonication for two hours. Upon having filtered it under vacuum, the samples under chemical-physical checking were introduced.

The experiment was repeated with solutions containing the three principles (melatonin, lutein and ectoine) at various concentrations, from 0.1 to 0.9%, always attaining a stable bonding between nanofibrils and active principles.

The mixtures thus yielded were then introduced into an emulsion (mere water solution+solubilised) and spread on depilated mice to verify the percutaneous absorption thereof.

Thus, it was found that:
a) a penetration of the chitin-active principle complex through the skin occurs,
b) chitin nanofibrils in no way harm cells, which go on behaving physiologically.
c) this type of structure facilitates the transdermal penetration of molecules, both liposoluble and water-soluble, serving also as stimulation for root-follicular (hair stem) cells.

This latter unexpected result demonstrates that the hair cycle stimulating action of the mixtures of substances according to the invention is potentiated when those are administered in the form of complexes with nanostructured chitin.

Conclusions

As it is clearly evident from all testing conducted both in vitro and in vivo, the antioxidants, the carotenoids (beta-carotene and lutein) and the lipoic acid and the immunostimulants, ectoine and beta-glucan, significantly enhance the bioprotective activity of melatonin. Mixtures of antioxidants and immunostimulants produce a melatonin-modulating effect with a high synergy of action making melatonin even more effective. Therefore, the above-reported mixtures carry out an interesting antiaging and anti-photoaging action on the skin, potentiating its defence mechanism towards exogenous and endogenous aggressions. also the activity carried out towards standard hair problems is interesting.

The invention claimed is:

1. A cosmetic composition for treatment of natural aging and photoaging of tissues and cutaneous annexes, the composition comprising: an excipient, pharmaceutically acceptable adjuvants and additives, and an effective amount of a mixture of substances comprising: (i) melatonin; (ii) at least one immunostimulant selected from the group consisting of ectoine, beta-glucan, and carboxymethyl betaglucan; and (iii) at least one antioxidant; wherein at least one of the substances of the mixture is adsorbed or bound to chitin nanofibrils; provided that the composition does not comprise tocotrienols.

2. The composition according to claim 1, wherein the antioxidant is selected from the group consisting of proanthocyanins, flavonoids, lipoic acid, vitamin A, beta-carotene, lutein, and zeaxanthin.

3. The composition according to claim 1, wherein the antioxidant is selected from the group consisting of carotenoids, polyphenols, lipoic acid, vitamin A, vitamin C, vitamin E, and coenzyme Q10.

4. The composition according to claim 1, wherein the antioxidant is selected from the group consisting of beta-carotene, lutein, zeaxanthin, lycopene, proanthocyanins, flavonoids, and polyphenols.

5. A method of treatment of natural aging and photoaging of tissues and cutaneous annexes comprising administration of the composition according to claim 1.

6. The method of treatment according to claim 5, for regenerating, hydrating and increasing the elasticity of cutaneous tissues, depigmenting of skin aging spots (age spots), and hair cycle boosting.

7. The method of treatment according to claim 5, wherein the composition is administered by topical application, or oral, intradermal or subcutaneous administration.

8. The composition according to claim 1 in a form selected from the group consisting of solution, colloidal solution, lotion, cream, macro- micro- or nanoemulsion, dispersion, gel, spray, foams, film, face mask, tablet, hard capsule, soft capsule, powder, granulate, and lyophilizate.

9. The composition according to claim 1 containing, by unitary dosage of application or administration, melatonin in an amount of from 1 mg to 10 mg.

10. The composition according to claim 9, wherein the weight ratio between melatonin and immunostimulant ranges from 1:0.005 mg to 1:50 mg and the weight ratio between melatonin and antioxidant ranges from 1:0.005 mg to 1:50 mg.

11. A method of preparing the composition according to claim 1, comprising mixing melatonin with each of immunostimulant and antioxidant in a ratio of from 1:0.005 to 1:50 mg.

12. A method for improving skin hydration and elasticity, modulating the skin surface lipid film, reducing the cutaneous roughness, decreasing the age spots, and improving the anagen/catagen ratio in hair growth cycle comprising administration of the composition according to claim 4.

13. A cosmetic composition for treatment of natural aging and photoaging of tissues and cutaneous annexes, the composition comprising: an excipient, pharmaceutically acceptable adjuvants and additives, and an effective amount of a mixture of substances consisting of: (i) melatonin and (ii) at least one immunostimulant selected from the group consisting of ectoine, beta-glucan, and carboxymethyl betaglucan; wherein at least one of the substances of the mixture is adsorbed or bound to chitin nanofibrils; provided that the composition does not comprise tocotrienols.

14. The composition according to claim 13 in a form selected from the group consisting of solution, colloidal solution, lotion, cream, macro- micro- or nanoemulsion, dispersion, gel, spray, foams, film, face mask, tablet, hard capsule, soft capsule, powder, granulate, and lyophilizate.

15. The composition according to claim 13 containing, by unitary dosage of application or administration, melatonin in an amount of from 1 mg to 10 mg.

16. A method of treatment of natural aging and photoaging of tissues and cutaneous annexes comprising administration of the composition according to claim 13.

17. The method of treatment according to claim 16, wherein the composition is administered by topical application, or oral, intradermal or subcutaneous administration.

18. A method of preparing the composition according to claim 13, comprising mixing melatonin with immunostimulant in a ratio of from 1:0.005 to 1:50 mg.

* * * * *